(12) United States Patent
Kuiper

(10) Patent No.: US 8,760,623 B2
(45) Date of Patent: Jun. 24, 2014

(54) INSPECTION APPARATUS FOR LITHOGRAPHY

(75) Inventor: Johannes Maria Kuiper, Koog aan de Zaan (NL)

(73) Assignee: ASML Netherlands B.V., Veldhoven (NL)

(*) Notice: Subject to any disclaimer, the term of this patent is extended or adjusted under 35 U.S.C. 154(b) by 996 days.

(21) Appl. No.: 12/746,071

(22) PCT Filed: Dec. 1, 2008

(86) PCT No.: PCT/EP2008/010176
§ 371 (c)(1),
(2), (4) Date: Aug. 6, 2010

(87) PCT Pub. No.: WO2009/071259
PCT Pub. Date: Jun. 11, 2009

(65) Prior Publication Data
US 2010/0302521 A1    Dec. 2, 2010

Related U.S. Application Data

(60) Provisional application No. 60/996,783, filed on Dec. 5, 2007.

(51) Int. Cl.
*G03B 27/42* (2006.01)
(52) U.S. Cl.
USPC ............................... 355/53; 355/63; 355/77
(58) Field of Classification Search
USPC ............... 355/27, 30, 53, 67, 71; 359/30, 31; 356/326, 328
See application file for complete search history.

(56) References Cited

U.S. PATENT DOCUMENTS

| 5,098,184 A * | 3/1992 | van den Brandt et al. ..... 353/102 |
| 2001/0033377 A1 | 10/2001 | Welch et al. |
| 2006/0066855 A1* | 3/2006 | Boef et al. .................... 356/401 |
| 2010/0226396 A1* | 9/2010 | Hollemann .................... 372/10 |

FOREIGN PATENT DOCUMENTS

| EP | 1 628 164 A2 | 2/2006 |
| FR | 2 661 255 A1 | 10/1991 |

OTHER PUBLICATIONS

International Search Report for Application No. PCT/EP2008/010176 mailed Mar. 12, 2009, 3 pgs.
Written Opinion for International Application No. PCT/EP2008/010176 mailed Jun. 17, 2010, 5 pgs.
Niu, Xinhui, "Specular Spectroscopic Scatterometry in DUV Lithography", *Proceedings of the SPIE*, Bellingham, VA, US, vol. 3677, Mar. 1, 1999, pp. 159-168.

\* cited by examiner

*Primary Examiner* — Steven H Whitesell Gordon
*Assistant Examiner* — Mesfin T Asfaw
(74) *Attorney, Agent, or Firm* — Sterne, Kessler, Goldstein & Fox P.L.L.C

(57) ABSTRACT

An illuminator configured to create a radiation beam for the metrology of a substrate surface includes an arc lamp, a parabolic reflector (150), a double cone (160) and a fly's eye integrator (110) in order to create a homogenized beam with a parabolic distribution.

34 Claims, 5 Drawing Sheets

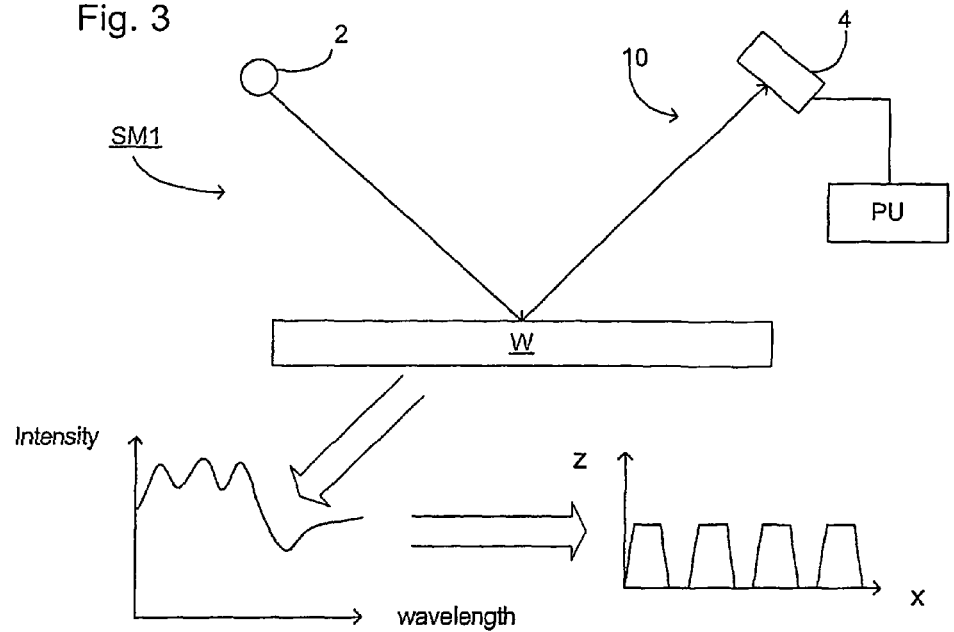
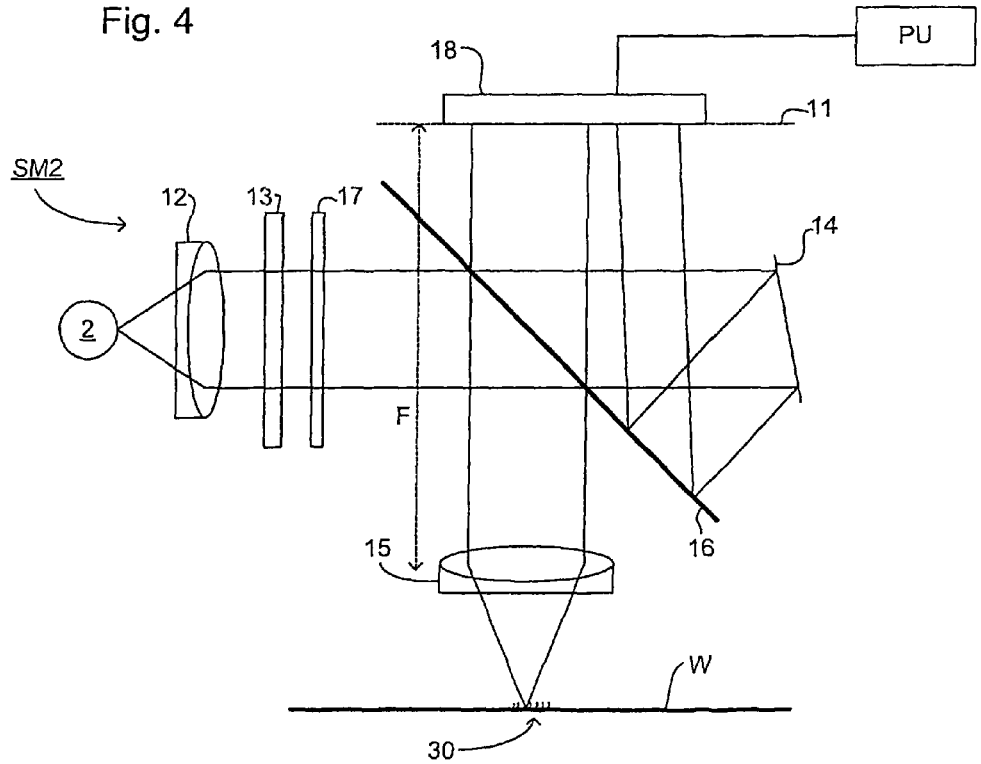

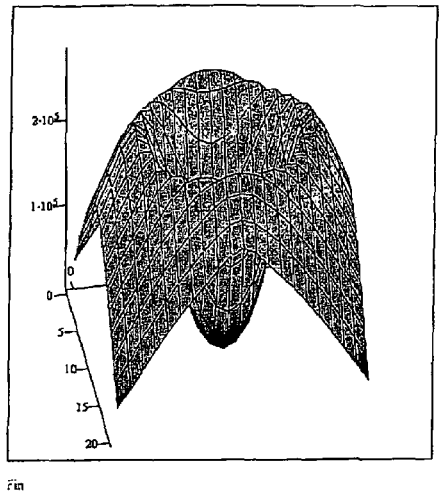 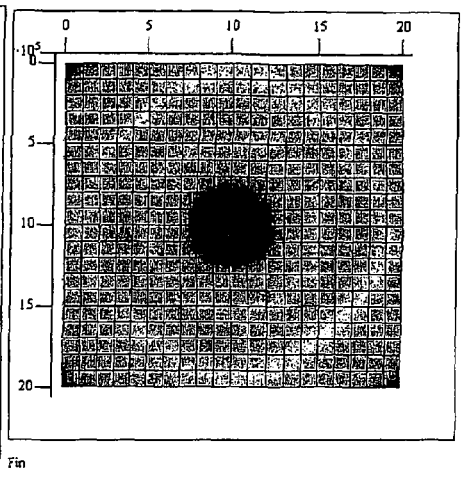
Fig. 7a          Fig. 7b
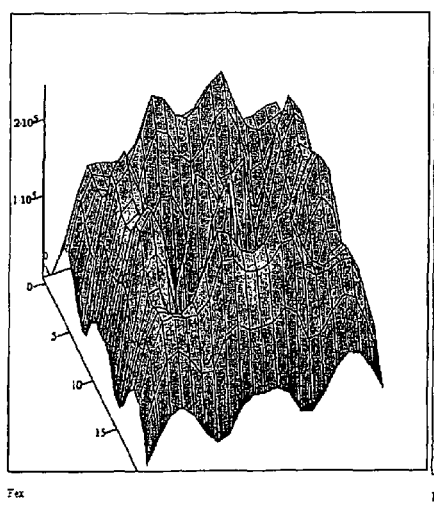 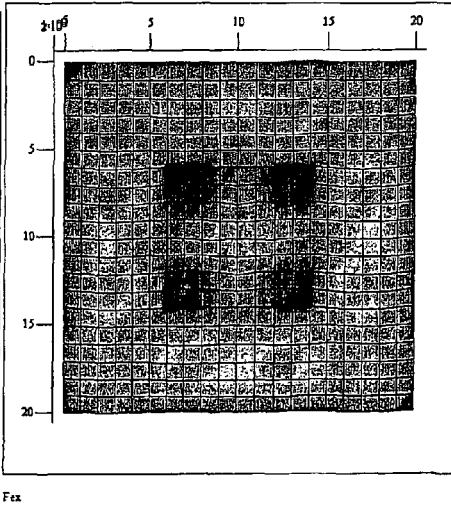
Fig. 8a          Fig. 8b

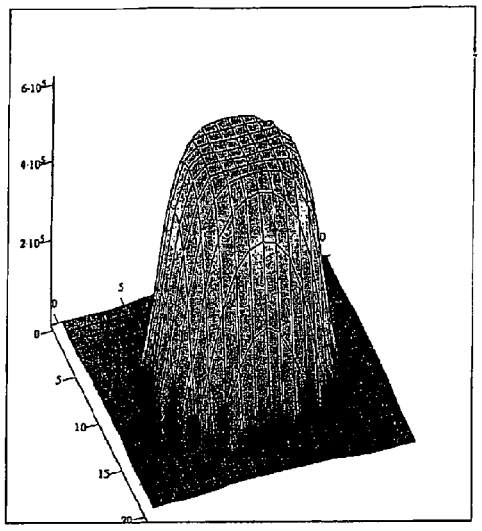
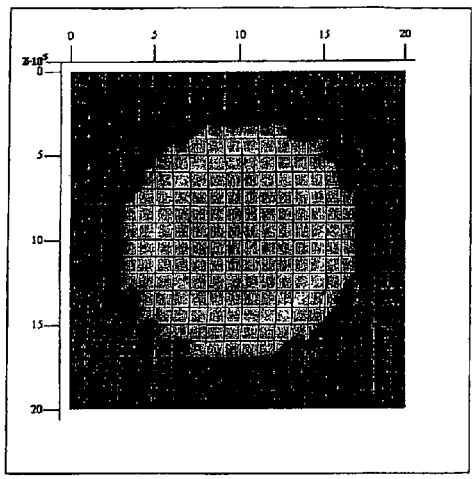
Fig. 9a  Fig. 9b
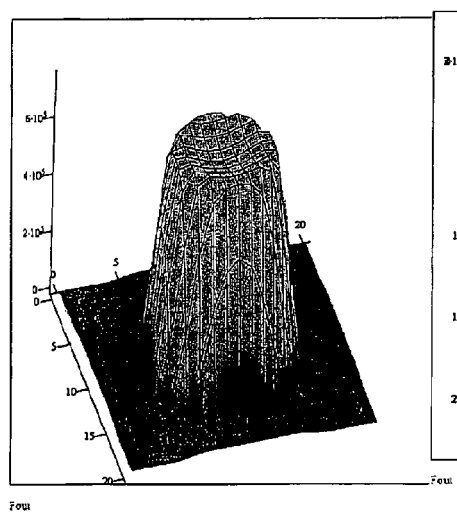
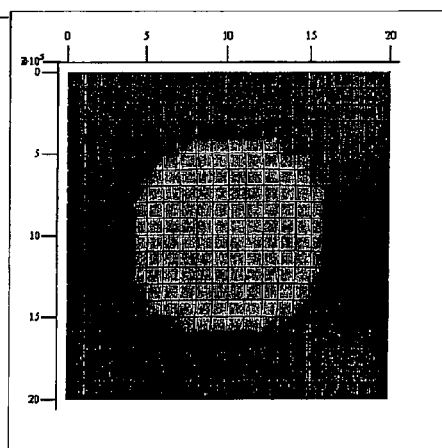
Fig. 10a  Fig. 10b

INSPECTION APPARATUS FOR LITHOGRAPHY

CROSS-REFERENCE TO RELATED APPLICATIONS

This application claims the benefit of U.S. provisional application 60/996,783, which was filed on 5 Dec. 2007, and which is incorporated herein in its entirety by reference.

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

An important consideration when creating beams for metrology measurement is the homogeneity of the beam. Optical systems such as lenses that have been used to focus the radiation beam have not generally contributed to the collimation of the beam; the output direction of travel of the radiation beam is dependent on the input direction of the beam, which may not have been homogenized in the first place.

In scatterometry, misalignments and overlay errors of properties of a substrate are determined by the reflected spectra of a radiation beam having been reflected from the substrate in question. In order that the reflected (and scattered) spectrum is a true representation of the surface of the substrate, it is desirable that the properties of the beam before it is reflected are also known. As measuring the properties of a beam interferes with it, it is desirable to make the beam to precise standards in the first place, with occasional measurements being possible to ensure that the properties of the beam have not changed. The most desirable property of an incident beam is that it is homogenous. Any inhomogeneity in the beam before it is reflected may contribute to inconsistencies in the reflected beam, which may be interpreted as effects caused by the surface of the substrate, rather than by inhomogeneities of the beam. This may lead to errors in the measurement of the surface of the substrate.

SUMMARY

It is desirable to provide a system for ensuring that the incident radiation beam in the scatterometer of the present invention is homogenous.

According to an aspect of the invention, there is provided an inspection apparatus, lithographic apparatus or lithographic cell configured to measure a property of a substrate, including: a radiation source configured to produce a radiation beam; a detector configured to detect the radiation beam once it has reflected from a surface to be measured; and an optical system configured to render a parabolic distribution to the radiation beam.

According to another aspect of the invention, there is provided a method of measuring a property of a substrate, including: providing a radiation beam; reflecting the radiation beam from a target on the substrate; detecting the reflection spectrum of the radiation beam reflected from the target; and determining a propery of the target on the substrate from the reflection spectrum, wherein providing the radiation beam includes rendering a parabolic distribution to the radiation beam.

According to another aspect of the invention, there is provided a device manufacturing method including: using a lithographic apparatus to form a pattern on a substrate; and determining a value related to a parameter of the pattern printed by: providing a radiation beam; reflecting the radiation beam from a target on the substrate; detecting the reflection spectrum of the radiation beam reflected from the target; and determining properties of the target on the substrate from the reflection spectrum, wherein providing the radiation beam includes rendering a parabolic distribution to the radiation beam.

According to an embodiment of the invention, there is provided a lithographic apparatus including an illumination optical system arranged to illuminate a pattern; a projection system arranged to project an image of the pattern onto a substrate; and an inspection apparatus configured to measure a property of the substrate, the inspection apparatus including an illumination system including a radiation source configured to produce a radiation beam, and an optical transmission system configured to render a parabolic distribution to the radiation beam, the radiation beam incident on a surface of the substrate; and a detector configured to detect the radiation beam reflected from the surface of the substrate.

According to an embodiment of the invention, there is provided a lithographic cell including a coater arranged to coat a substrate with a radiation sensitive layer; a lithographic apparatus arranged to expose an image onto the radiation sensitive layer of the substrate coated by the coater; a developer arranged to develop the image exposed by the lithographic apparatus; and an inspection apparatus configured to measure a property of the substrate, the inspection apparatus including an illumination system including a radiation source configured to produce a radiation beam, and an optical transmission system configured to render a parabolic distribution to the radiation beam, the radiation beam incident on a surface of the substrate; and a detector configured to detect the radiation beam reflected from the surface of the substrate.

According to an embodiment of the invention, there is provided a device manufacturing method including forming a pattern on a substrate using a lithographic apparatus; and determining a value related to a parameter of the pattern formed on the substrate by providing a radiation beam; reflecting the radiation beam from a target on the substrate; detecting the reflection spectrum of the radiation beam reflected from the target; and analyzing the reflected spectrum to determine the value related to the parameter, wherein providing the radiation beam includes rendering a parabolic distribution to the radiation beam.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 3 depicts a first scatterometer in accordance with an embodiment of the invention;

FIG. 4 depicts a second scatterometer in accordance with an embodiment of the invention;

FIGS. 7a, 8a, 9a and 10a depict 3-D reconstructions of the image planes of the radiation beam at various positions in the set up of FIG. 5; and FIGS. 7b, 8b, 9b and 10b depict pixel maps of each of the respective radiation beam images of FIGS. 7a, 8a, 9a and 10a.

DETAILED DESCRIPTION

Figure 1:
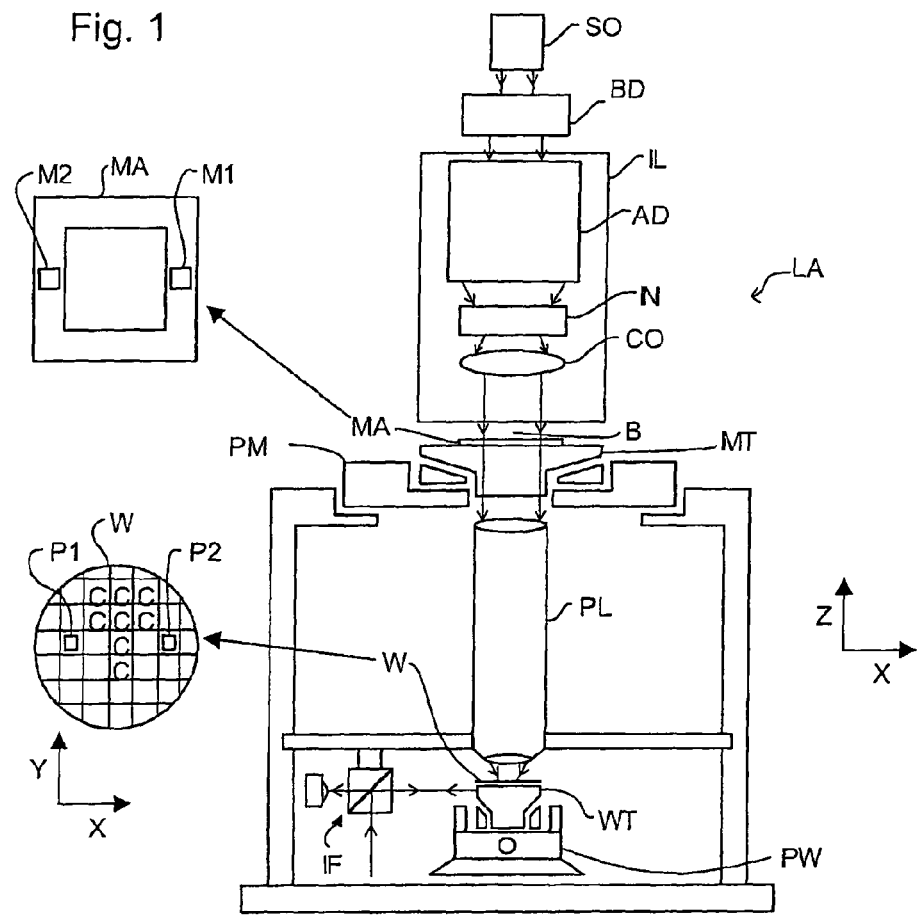
FIG. 1 depicts a lithographic apparatus in accordance with an embodiment of the invention.

FIG. 1 schematically depicts a lithographic apparatus. The apparatus includes an illumination system (illuminator) IL configured to condition a radiation beam B (e.g. UV radiation or DUV radiation); a patterning device support or support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support or support structure holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the patterning device support or support structure (e.g., mask table) MT, and is patterned by the patterning device. Having traversed the patterning device (e.g. mask) MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device (e.g. mask) MA with respect to the path of the radiation beam B, e.g. after mechanical retrieval from a mask library, or during a scan. In general, movement of the patterning device support or support structure (e.g. mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support or support structure (e.g. mask table) MT may be connected to a short-stroke actuator only, or may be fixed. Patterning device (e.g. mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g. mask) MA, the mask alignment marks may be located between the dies.

The depicted apparatus could be used in at least one of the following modes:

1. In step mode, the patterning device support or support structure (e.g. mask table) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support or support structure (e.g. mask table) MT and the substrate table WT are scanned synchronously while a pattern imparted to the radiation beam is projected onto a target portion C (i.e. a single dynamic exposure). The velocity and direction of the substrate table WT relative to the patterning device support or support structure (e.g. mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support or support structure (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
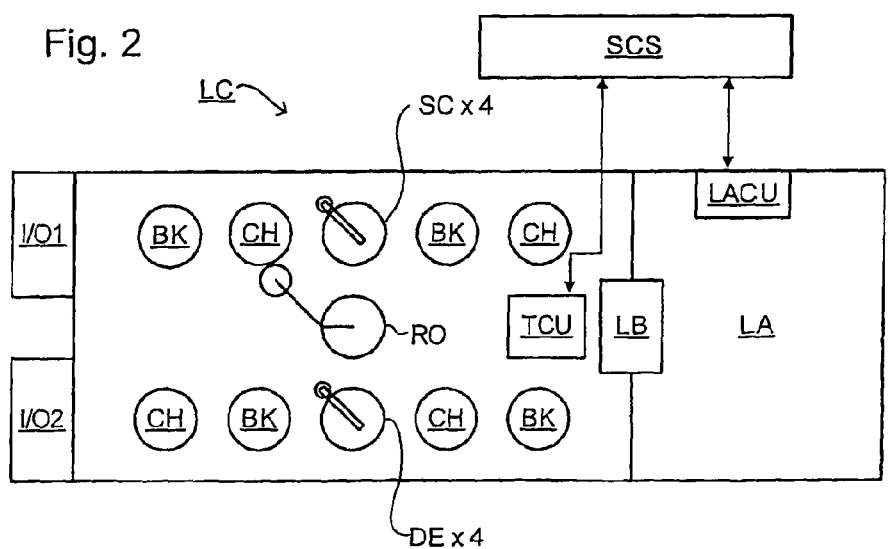
FIG. 2 depicts a lithographic cell or cluster in accordance with an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 3 depicts a scatterometer SM1 which may be used in an embodiment of the present invention. It includes a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer SM2 that may be used in an embodiment of the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than including a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$, and a spacing of at least 2 $\delta\lambda$ (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

Figure 5:
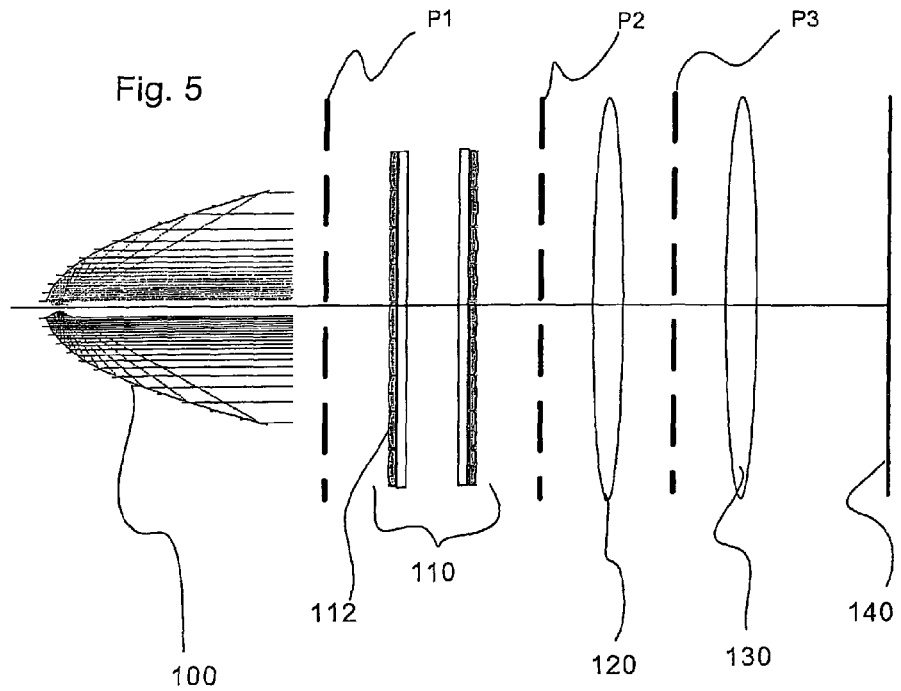
FIG. 5 depicts a set up for creating a parabolic radiation beam according to an embodiment of the invention.

FIG. 5 shows an embodiment of an illuminating system including a xenon arc lamp 100 with a parabolic reflective exterior; a fly's eye integrator 110; a telecentric lens 120; an imaging lens 130 and an image plane 140 representing the position at which the radiation beam is effectively focused on the substrate. The radiation beam will then reflect off of the substrate and be detected by a detector, also in an image plane such that the radiation reflected from the substrate is again focused as it is detected. The imaging lens 130 and image plane 140 are not essential elements of the illumination system. Their purpose is for measurement, in particular to enlarge the image at position P2 as shown in FIG. 5 to an appropriate size and format to enable spatial and angular homogeneity analysis.

The radiation source need not be a xenon arc lamp, but a xenon arc lamp may be used that is a standard arc lamp that produces radiation by an electric (or voltaic) arc. The lamp may be a mercury (Hg) arc source lamp or a lamp tuned to any other UV source. The aim is to obtain maximum brightness from the lamp. The skilled person will recognize what alternative UV sources will be suitable for this purpose.

The arc lamp 100 as shown consists of two electrodes typically made of tungsten which are separated by a gas in a bulb. The preferred gas in this case is xenon, though the bulb may also contain neon, argon, krypton, sodium, metal halide or mercury, for example. A benefit of using xenon is that a bright white radiation or light is created that closely mimics natural daylight, including a large array of wavelengths. The radiation emitted from the xenon arc lamp also has the benefit of producing a high proportion of radiation in the UV-range of the radiation spectrum. The electric arc in the arc lamp consists of gas which is initially ionized by a voltage and is therefore electrically conductive. To start the arc lamp, usually a very high voltage is needed to ignite the arc.

An embodiment of the present arc lamp has a distance between the electrodes of about 1.3 mm. Alternatively, the distance between the electrodes may be as small as about 0.8 mm and may be a Hamamatsu or a Ushio radiation source, which vary between about 0.8 and 1.3 mm in arc length. In fact, any arc length or plasma configuration may be used; even a toroid plasma source that produces UV. The arc length is thereby dependent on the gas or plasma used and other features of the lamp that limit how far the arc will jump from one electrode to the other.

The anode in an arc lamp is typically larger than the cathode. When this is the case, the anode may be positioned at the exit side of the xenon arc lamp in order to increase the likelihood of all radiation that is created from the xenon arc lamp being reflected from the parabola. It is preferred that as much radiation as possible is reflected from the parabolic reflector, as it may subsequently be diverted or blocked as required. In some embodiments, an obscuration shim may also be used and this may also be placed at the exit of the parabolic reflector. Specifically, numerical aperture (NA) selection may be carried out with a shim plate containing an annulus (i.e. an annular transmission shape) at the parabola exit. Alternatively, an ellipsoid optical transmission device (e.g. an aperture or a lens device) may be used to re-image the source in a more convenient position for finer spatial and angular (i.e. NA) tuning of the radiation beam.

As mentioned above, the xenon arc lamp may be surrounded by a parabolic reflector. A parabolic reflector is a reflective device that is generally in the shape of a paraboloid of revolution. The thermo-mechanical stability of the arc with respect to the parabola is key. The parabola may be a "cold light" reflector that transmits infra-red radiation.

As can be seen in FIG. 5, radiation that is emitted at the focus which reflects from the inner surface of the parabolic reflector will be emitted from the open end of the reflector in parallel rays. The parallel rays are furthermore parallel to the axis of the parabolic reflector, the axis being shown as the horizontal line going through the reflector 100 in FIG. 5. The parabolic reflector may alternatively be referred to as a cylindrical arc radiation source envelope. This envelope may be made from aluminum or coated in aluminum and have a window for exiting light to leave the envelope. Alternatively, the parabolic reflector may have a coat that is made of aluminum and gold or aluminum and another coating. The window tunes the exit etendue to the fly's eye integrators 110 for optimum special and angular homogenization.

The plane labeled P1 is positioned such that a detector at this plane would show the radiation emitted from the parabolic reflector. An image of the radiation at this plane is shown in FIGS. 7a and 7b.

Enlarging the parabola of the parabolic reflector reduces the numerical aperture (NA) of the beam and improves homogeneity. Specifically, enlarging the parabola with respect to the arc size reduces the NA spread after reflection from the parabola. This makes the system as a whole less sensitive to plasma intensity variations and to displacement of the plasma burning point with regard to the arc. Enlarging the parabola also reduces overheating, by spreading the heat load over wider area.

The next element in the illuminator is the fly's eye integrator 110. A fly's eye integrator is made up of an array of small lenses that are convex on a first side (the side facing the incoming radiation) and flat on the other. The first side may be aspherical or any shape or orientation that still fulfils the requirements of the fly's eye integrator. The purpose of the small lenses is to focus parallel incoming rays onto a point. The size of the lenses is usually chosen such that the focal point is on the flat rear surface of the array. However, the skilled person will understand that the focal point can be anywhere downstream of the array of small lenses that enables a focused image to be detected and/or used for measurement. The small lenses are hereinbelow referred to as lenslets.

The fly's eye integrator 110 of an embodiment of the present invention is preferably made of two sets of lenslets 112 facing in opposite directions as shown in FIG. 5. The first set is an array of lenslets with their convex side facing the incoming radiation from the parabolic reflector. The two sets of lenslets have their flat sides facing each other. Preferably, two lenslets that are positioned back-to-back have coincident focal points such that the radiation that is parallel when it is input into the upstream array of lenslets remains parallel as it exits the second array of lenslets. The beam exiting the second array of lenslets will, by the effect of being focused and re-diverged, be more homogeneous than when entering the first array because stray beams will have been either focused or reflected, and thus eliminated from the output beam. The respective sizes and focal lengths of the arrays of lenslets may be chosen to determine the size of the output beams.

The lenslets are generally convex. However, they do not have to be spherical. The lenslets 112 may be aspherical, with the asphericity being tuned to the exit NA of the parabola. In terms of cross-section when viewed along the direction of the beam transmission, the lenslets 112 may be circular. The diameter of the cross-section of the lenslets may be adjusted to optimize the size of the lenslet array such that a maximum amount of radiation is transmitted. An optimum array size may be about 5×5 mm$^2$, according to experimental evidence aiming to determine a balance between homogeneity of the beam and the percentage of radiation transmitted. Alternatively, the lenslets 112 may be square. Square lenslet arrays have the highest transmission of radiation, with hexagonally packed circular lenslets 112 having second highest transmission and finally circular lenslets 112 that are square packed allowing the least transmission. An alternative arrangement is to use hexagonal lenslets 112. Two oppositely-facing arrays of lenslets 112 is referred to hereinbelow as a single fly's eye integrator. Two (or more, for example four) fly's eye integrators may also be used to homogenize both the object and the conjugate planes.

As an alternative embodiment, a system may be envisaged that includes no fly's eye at all, but uses annular NA selection from the parabola using a shim or similar as described above. Optionally, a shim may have an annulus that is tuned such that the NA is very small and can be refolded by a double folding cone (described below in association with FIG. 6) to an even smaller diameter. Folding the annular beam further raises the NA for etendue conservation reasons. At a moving sensor, the beam can be converged by a lens into a fiber mode scrambler (or tapered homogenizing rod or similar) in order to attain NA homogeneity.

As mentioned above, the centre of the fly's eye integrator may be blocked by an obscuration shim. Alternatively, the centre ring of a series of concentric rings of lenslets 112 may be opaque to block stray light from the lamp. Yet further, centre lenslets of the array of lenslets may be missing. Either method of preventing transmission of light through the centre of the array of lenslets 112 or incorporating an obscuration shim into the centre of the parabolic reflector enables stray light from the lamp to be blocked, creating an annular output beam which reduces overlap of diffraction spectra when diffracted and improves diffraction spectra measurements. Alternatively or additionally, the annular beam may be further compressed to increase homogeneity. Outer rays of radiation have higher diffractive orders than inner rays because of their larger azimuth angle when reflecting from the parabolic reflector. Higher orders have more information, which is useful for later measurement in the optical system of the scatterometer.

Some of the radiation from the lamp may be lost when the centre rays are blocked and so it is desirable to balance the use of an obscuration shim or opacity of lenslets 112 (and thereby increasing homogeneity and usefulness of the beam) with using as much radiation as possible.

The radiation, once it has been transmitted through the fly's eye integrator 110 and deflected by the lenslets 112, will take on a different distribution from the radiation that has exited the parabolic reflector. The light intensity distribution as would be in the plane labeled P2 is shown in FIGS. 8a and 8b.

A carousel (color wheel) of interference filters may be provided before (i.e. upstream in the radiation beam direction of transmission), in the middle of (i.e. between the arrays), or after (i.e. downstream of) the fly's eye integrator 110 for wavelength selection. The selected wavelengths will thereby enter the telecentric lens 120. A telecentric lens 120 is a compound lens which enables the rays through the centre of the entrance or exit pupil to be parallel to the optical axis. In other words, a telecentric lens 120 has the same magnification for all distances, rather than different magnifications for light coming from different distances (i.e. from slightly different angles). This gets rid of stray rays of radiation that might be coming into the system at un-parallel angles. The distribution of the radiation upon exiting the telecentric lens 120 and as would be detected at plane P3 is shown in FIGS. 9a and 9b.

As shown in FIG. 5, the radiation may optionally pass through the optional imaging lens 130. The imaging lens 130 basically focuses the radiation beam yet further for reflecting from the substrate surface in the scatterometer. The radiation as detected on the imaging plane 140 is shown in FIGS. 10a and 10b. The resultant radiation distribution shows a parabolic intensity distribution in FIG. 10a. As the lens 130 and the plane 140 are not essential to the invention, the images as shown in FIGS. 10a and 10b may not necessarily exist. Indeed, these figures show some spherical aberration which would need to be corrected for (e.g. using the homogenizing rod as described below)

Figure 6:
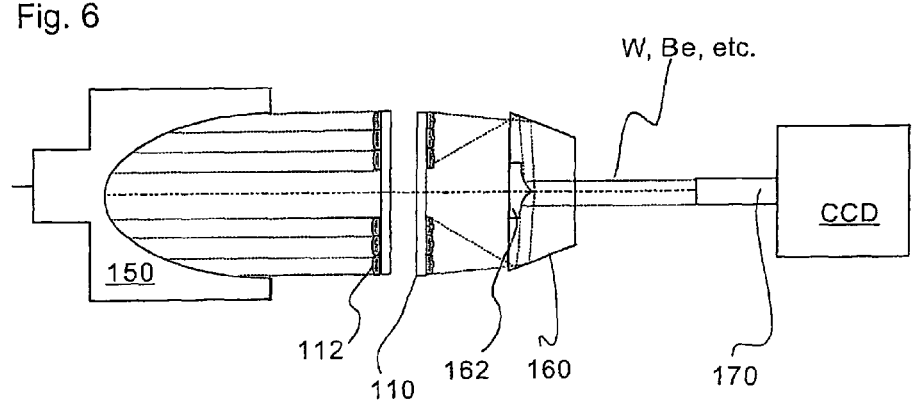
FIG. 6 depicts a set up for creating a parabolic radiation beam according to an embodiment of the invention.

FIG. 6 shows a setup according to an embodiment of the invention. Specifically, the parabolic reflector 150 reflects the radiation beam in parallel onto the lenslets 112 of the fly's eye integrator 110. The fly's eye integrator 110 of FIG. 6 is missing the central lenslets 112 to indicate the lack of transmission of radiation through the centre of the fly's eye integrator.

A first element that is shown in FIG. 6 and that is present in the second embodiment is a double cone 160. The double cone 160 has an internally reflective surface of a larger cone which reflects the radiation that is output from the lenslets 112 of the fly's eye integrator 110 onto a central, smaller cone 162, thus focusing the homogenous radiation into a narrower (pencil-shaped) beam as shown in the Figure. This double cone element 160 effectively refolds the annular beam coming from the fly's eye integrator into a pencil shape and allows expansion of the parabola.

There are several shapes that the double cone may take. A first is shown in FIG. 6, wherein the surface of the internal cone in fact has a concave conical surface. A straight conical surface may alternatively be used. The outer cone 160 with the internal reflective surface may have straight edges as shown in FIG. 6, or the surfaces that reflect the beam may be curved, with a concave surface facing inwards to focus the reflecting beam. The two cones of the double cone element will be shaped in order to reflect the largest amount of radiation and also to refold the annular beam into the desired pencil shape.

As an alternative embodiment, a cone may not be used, but a large diameter lens with a stronger focusing value will be needed at a moving sensor aperture in order to converge a resultant quasi-parallel beam into either a tapered glass rod (tapering away from the incoming beam), a scattering bar or a tapered (internal mirror) cone to fold the etendue into a smaller area with a larger NA.

The second element that FIG. 6 contains that is not in the first embodiment is a homogenizing rod 170. This may be a scatter bar, a homogenizing rod or even a fiber mode scrambler that may be applied as an additional NA homogenizer device at the entrance window of a detector box. This is optional and may be used depending on the requirements of the output beam before the sensor CCD. The fly's eye integrator should yield a spatially homogeneous beam, but an additional homogenizing rod or similar may assist in additional NA homogeneity if needed.

The homogenizing rod may be a standard beam homogenizer that smoothes out irregularities and beam profile to create a more uniform profile. One example of a homogenizer or homogenizing rod may be in multifaceted mirror with square facets that reflects radiation at different angles to create a beam with uniform power across the whole beam profile (known as a "top hat" profile). The homogenizer may be tapered or have any other shape adapted for etendue manipulation. Alternatively, the NA homogenizer may be a fiber mode scrambler on top of a moving sensor with a focusing lens in front of the scrambler. The focusing lens converges the parallel radiation coming from the fly's eye telecentric lens 120 (or curved cone element 160) into the fiber of the mode scrambler. The sensor can thus move freely and still receive the beam of spatially homogeneous light. At the sensor, the light is made angularly homogeneous.

Yet furthermore, spatial and NA homogeneity may be created each at a desired tunable level in an arbitrary sequence; i.e. at any position in the apparatus. This includes the obscuration shim or ellipsoid for repositioning the beam. Other homogenizing methods may be determined by the person skilled in the art.

A further device that may be included in the system is most useful when the illumination apparatus is in a fixed position but the sensor moves relatively to this fixed position. The further device is a bellow Be (or a set of bellows) that is positioned between the fixed parts (e.g. up to the double cone segment) and the moving parts (the sensor with the homogenizer). The bellow Be may be used to expel the influence of turbulent air flow on the homogeneity of the radiation beam by causing all of the air in the area to travel in the same direction, thus eliminating or at least reducing turbulence. The bellow surrounds the radiation beam and is folded or unfolded (like a bellow in a classical camera or a concertina) in an axial direction when the sensor moves closer or away from the illumination apparatus. The airflow that may contain turbulence thus flows around the bellow and out of the way of the radiation beam.

In a set-up process, the illumination system will be as shown in FIG. 6. When this illumination system is incorporated into a scatterometer as described above, the illuminator takes the place of the radiation source 2 but the detector CCD shown in FIG. 6 is replaced by the detector 10,18 of the scatterometer. The homogenizing rod in this case is positioned upstream of the substrate W.

The result of the illumination system as shown in FIG. 5 or 6 is that a higher-intensity radiation beam is thereby created, enabling a higher throughput than previously known.

The sensor CCD,10,18 may move while the illuminator is static in order to obtain a full pixel map as shown in FIGS. 7b, 8b, 9b and 10b. It may be possible to couple the illuminator and the sensor using fiber optics. However, there is the risk that the fiber optics may lose some of the intensity of the radiation beam and potentially reduce homogeneity. The aim, on the other hand, is to collimate the radiation beam well enough such that it may be focused on the entrance of the homogenizing rod. Alternatively, the movement of the sensor and the fly's eye integrator may be carefully synchronized such that the collimated and homogenized beam is always directed in the correct area of the detector CCD, 10, 18 without having to use further beam-directing elements.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. An inspection apparatus comprising:
an optical transmission system configured to render a parabolic distribution to a radiation beam, the radiation beam being incident on a surface of a substrate,
wherein the optical transmission system comprises:
a fly's eye integrator comprising an array of concentric rings of lenslets, the array of concentric rings of lenslets comprising a central ring that is opaque, and
a double cone element arranged downstream of the fly's eye integrator; and
a detector configured to detect the radiation beam reflected from the surface of the substrate.

2. The inspection apparatus according to claim 1, wherein the optical transmission system further comprises:
a parabolic reflector; and
a lens.

3. The inspection apparatus according to claim 2, wherein the parabolic reflector comprises an arc lamp envelope with a window in its center, the arc lamp envelope being shaped to tune an exit etendue of the parabolic radiation beam to the fly's eye integrator.

4. The inspection apparatus according to claim 3, wherein the arc lamp envelope surface comprises aluminum.

5. The inspection apparatus according to claim 2, wherein the lens is a telecentric lens.

6. The inspection apparatus according to claim 2, wherein the lens is an imaging lens.

7. The inspection apparatus according to claim 2, wherein the lens comprises:
a telecentric lens component; and
an imaging lens component.

8. The inspection apparatus according to claim 1, wherein the double cone element is configured to refold an annular radiation beam into a pencil shape.

9. The inspection apparatus according to claim 1, wherein the fly's eye integrator comprises another array of concentric rings of lenslets oppositely-facing the array of concentric rings of lenslets.

10. The inspection apparatus according to claim 1, wherein a lenslet of the array of concentric rings of lenslets is aspherical.

11. The inspection apparatus according to claim 10, wherein the asphericity of the lenslet of the array of concentric rings of lenslets is tuned to an exit numerical aperture (NA) of a parabolic reflector.

12. The inspection apparatus according to claim 1, wherein a lenslet of the array of concentric rings of lenslets is square if viewed from the radiation source.

13. The inspection apparatus according to claim 1, wherein a lenslet of the array of concentric rings of lenslets is circular if viewed from the radiation source.

14. The inspection apparatus according to claim 1, wherein at least some lenslets of the array of concentric rings of lenslets are square-packed.

15. The inspection apparatus according to claim 1, wherein at least some lenslets of the array of concentric rings of lenslets are hexagonally-packed.

16. The inspection apparatus according to claim 1, wherein a lenslet of the array of concentric rings of lenslets is hexagonal if viewed from the radiation source.

17. The inspection apparatus according to claim 1, further comprising a carousel of interference filters configured to allow specific wavelengths of the radiation beam to be transmitted to the surface of the substrate.

18. The inspection apparatus according to claim 17, wherein the carousel of interference filters is positioned:
   upstream of the fly's eye integrator;
   between a pair of lenslet arrays of the fly's eye integrator; or
   downstream of the fly's eye integrator.

19. The inspection apparatus according to claim 1, wherein the radiation source is an arc lamp.

20. The inspection apparatus according to claim 19, wherein the arc lamp has an arc length of between about 0.8 and 1.3 mm.

21. The inspection apparatus according to claim 19, wherein the arc lamp comprises a first and second electrode, the first electrode being larger than the second electrode and positioned at an exit side of a parabolic reflector.

22. The inspection apparatus according to claim 1, further comprising a homogenizing rod positioned between the fly's eye integrator and the detector.

23. The inspection apparatus according to claim 1, further comprising an optical system configured to transmit the radiation beam reflected from the surface of the substrate to the detector.

24. An inspection method comprising:
   reflecting a radiation beam from a target on a substrate, the radiation beam comprising a parabolic distribution formed by an optical transmission system, the optical transmission system comprising:
      a fly's eye integrator, and
      a double cone element arranged downstream of the fly's eye integrator,
   wherein forming of the parabolic distribution of the radiation beam comprises:
      reflecting the radiation beam off a parabolic reflector, and
      transmitting the radiation beam reflected from the anabolic reflector through the fly's eye integrator and a lens, the transmitting comprising blocking a central portion of the radiation beam to prevent stray radiation from being detected;
   detecting a reflection spectrum of the radiation beam reflected from the target; and
   determining a property of the target on the substrate from the reflection spectrum.

25. The method according to claim 24, wherein the forming of the parabolic distribution of the radiation beam further comprises:
   creating, using the double cone element, an annular radiation beam; and
   refolding, using the double cone element, the annular radiation beam into a pencil shape.

26. The method according to claim 24, wherein the transmitting of the reflected radiation beam through the fly's eye integrator further comprises transmitting the radiation beam through a pair of oppositely-facing arrays of lenslets.

27. The method according to claim 24, wherein a carousel of interference filters is used for transmission of specific wavelengths of the radiation beam.

28. The method according to claim 24, further comprising homogenizing the radiation beam.

29. The method according to claim 24, wherein the property comprises:
   an overlay error between two layers formed on the substrate; or
   a critical dimension of a feature on the substrate.

30. A lithographic apparatus comprising:
   an illumination optical system configured to illuminate a pattern;
   a projection system configured to project an image of the pattern onto a substrate; and
   an inspection apparatus configured to measure a property of the substrate, the inspection apparatus comprising:
      an illuminator comprising:
         a radiation source configured to produce a radiation beam, and
         an optical transmission system configured to render a parabolic distribution to the radiation beam, the radiation beam being incident on a surface of the substrate, wherein the optical transmission system comprises:
            a fly's eye integrator comprising an array of concentric rings of lenslets, wherein a central ring of the array of concentric rings lenslets is opaque, and
            a double cone element arranged downstream of the fly's eye integrator; and
      a detector configured to detect the radiation beam reflected from the surface of the substrate.

31. A lithographic cell comprising:
   a coater configured to coat a substrate with a radiation sensitive layer;
   a lithographic apparatus configured to expose an image onto the radiation sensitive layer of the substrate;
   a developer configured to develop the image exposed by the lithographic apparatus; and
   an inspection apparatus configured to measure a property of the substrate, the inspection apparatus comprising:
      an illumination system comprising:
         a radiation source configured to produce a radiation beam, and
         an optical transmission system configured to render a parabolic distribution to the radiation beam, the radiation beam being incident on a surface of the substrate, wherein the optical transmission system comprises:
            a fly's eye integrator comprising an array of concentric rings of lenslets, wherein a central ring of the array of concentric rings of lenslets is opaque, and
            a double cone element arranged downstream of the fly's eye integrator; and
      a detector configured to detect the radiation beam reflected from the surface of the substrate.

32. A device manufacturing method comprising:
   forming a pattern on a substrate using a lithographic apparatus; and determining a value related to a parameter of the pattern formed on the substrate, the determining comprising:
reflecting a radiation beam from a target on the substrate, the radiation beam comprising a parabolic distribution formed by an optical transmission system, wherein forming of the parabolic distribution of the radiation beam comprises:
reflecting the radiation beam off a parabolic reflector, and
transmitting the radiation beam reflected from the parabolic reflector through a fly's eye integrator and a lens, the transmitting comprising blocking a central portion of the radiation beam to prevent stray radiation from being detected;
detecting a reflection spectrum of the radiation beam reflected from the target; and
analyzing the reflected spectrum to determine the value related to the parameter.

33. An inspection apparatus comprising:
an illumination system comprising:
a radiation source configured to produce a radiation beam, and
an optical transmission system configured to render a parabolic distribution to the radiation beam comprising a fly's eye integrator, the fly's eye integrator comprising an array of concentric rings of lenslets, wherein a central ring of the array of concentric rings of lenslets is opaque; and
a detector configured to detect the radiation beam reflected from the surface of the substrate.

34. A method comprising:
reflecting a radiation beam from a target on a substrate, the radiation beam comprising a parabolic distribution;
detecting a reflection spectrum of the radiation beam reflected from the target; and
determining a property of the target on the substrate from the reflection spectrum,
wherein the parabolic distribution of the radiation beam is produced by
reflecting the radiation beam off a parabolic reflector; and
transmitting the reflected radiation beam through a fly's eye integrator and a lens, the transmitting comprising blocking a central portion of the radiation beam to prevent stray radiation from being detected.

* * * * *

UNITED STATES PATENT AND TRADEMARK OFFICE
CERTIFICATE OF CORRECTION

PATENT NO. : 8,760,623 B2
APPLICATION NO. : 12/746071
DATED : June 24, 2014
INVENTOR(S) : Johannes Maria Kuiper It is certified that error appears in the above-identified patent and that said Letters Patent is hereby corrected as shown below:

In the Claims

Column 15, lines 54-55, claim 24, after "from the", delete "anabolic" and insert --parabolic--.

Signed and Sealed this
Fourth Day of November, 2014

Michelle K. Lee
*Deputy Director of the United States Patent and Trademark Office*